US00PP26052P3

(12) United States Plant Patent
Carruth

(10) Patent No.: US PP26,052 P3
(45) Date of Patent: Nov. 10, 2015

(54) HYBRID TEA ROSE PLANT NAMED 'WEKGOBAFA'

(50) Latin Name: *Rosa hybrida*
Varietal Denomination: WEKgobafa

(71) Applicant: Early Morning LLC, Pomona, CA (US)

(72) Inventor: Thomas F. Carruth, Altadena, CA (US)

(73) Assignee: EARLY MORNING LLC, Pomona, CA (US)

( * ) Notice: Subject to any disclaimer, the term of this patent is extended or adjusted under 35 U.S.C. 154(b) by 98 days.

(21) Appl. No.: 13/998,681

(22) Filed: Nov. 22, 2013

(65) Prior Publication Data

US 2015/0150164 P1 May 28, 2015

(51) Int. Cl.
*A01H 5/02* (2006.01)

(52) U.S. Cl.
USPC ..... Plt./135

(58) Field of Classification Search
USPC ..... Plt./101, 130, 135
See application file for complete search history.

(56) References Cited

U.S. PATENT DOCUMENTS

PP10,071 P 10/1997 Carruth
PP17,305 P2 12/2006 Carruth

*Primary Examiner* — Susan McCormick Ewoldt
(74) *Attorney, Agent, or Firm* — McKee, Voorhees & Sease, PLC

(57) ABSTRACT

A new variety of Hybrid Tea rose suitable for garden decoration, having flowers of deep golden orange coloration finished with a kiss of red.

1 Drawing Sheet

Classification: The present invention relates to a new *Rosa hybrida* plant.

Variety denomination: The new plant has the varietal denomination 'WEKgobafa'.

BACKGROUND OF THE INVENTION

This invention relates to a new and distinct variety of Hybrid Tea Rose. It has as its seed parent the variety known as 'KORberbeni' (not patented) and as its pollen parent the variety known as 'WEKosupalz' (U.S. Plant Pat. No. 17,305).

SUMMARY OF THE INVENTION

Among the features which distinguish the new variety from other presently available and commercial rose cultivars known to the inventor are the following combinations of characteristics: its unusual deep golden orange coloration finished with a kiss of red, its many stipitate glands and some hairs on the peduncle and its abundant blooms on long cutting stems. The plant has an upright moderately spreading growing habit, suitable for outdoor garden decoration.

Asexual reproduction of the new variety by budding as performed in Kern County and Pomona, Calif., shows that the foregoing and other distinguishing characteristics come true to form and are established and transmitted through succeeding asexual propagations. 'WEKgobafa' may be asexually propagated by cuttings, budding and grafting. The budding and grafting successfully occurred on the plant/rootstock *Rosa hybrida* cv. Dr. Huey (not patented).

COMPARISON WITH PARENTS

The new rose may be distinguished from its seed parent, 'KORberbeni' by the following combination of characteristics: whereas 'WEKgobafa' bears double flowers (about 27 to 35 petals) of deep golden orange coloration finished with a kiss of red, 'KORberbeni' bears double flowers of golden yellow coloration with significantly lesser petalage (about 17 to 25 petals). The new variety is classified as a Hybrid Tea rose with an upright moderately spreading tall growing habit (about 120 to about 200 cm. in height), whereas the seed parent is classified as a Grandiflora rose with a shorter growing habit (about 150 cm. in height).

The new variety may be distinguished from its pollen parent, 'WEKosupalz' by the following combination of characteristics: whereas 'WEKgobafa' bears double flowers (about 27 to 35 petals) of deep golden orange coloration finished with a kiss of red, 'WEKosupalz' bears double flowers of golden orange coloration with a bronzy red reverse with lesser petalage (about 26 to 30 petals). The new variety is classified as a Hybrid Tea rose with an upright moderately spreading growing habit (about 120 to about 200 cm. in height), whereas the pollen parent is classified as a Grandiflora rose with a very upright taller growing habit (about 170 to about 200 cm. in height).

COMPARISON WITH THE CLOSEST COMMERCIALLY AVAILABLE CULTIVAR

The new variety may be distinguished from its closest commercially available cultivar, 'WEKjuvoo' (U.S. Plant Pat. No. 10,071) by the following combination of characteristics: whereas 'WEKgobafa' bears double flowers (about 27 to 35 petals) of deep golden orange coloration finished with a kiss of red, 'WEKjuvoo' bears double flowers of bright orange-yellow coloration blushed red with heavier petalage (about 34 to 38 petals). The new variety has an upright moderately spreading tall growing habit (about 120 to about 200 cm. in height), whereas the closest commercially available cultivar has a bushy upright shorter growing habit (about 120 to 155 cm. in height).

BRIEF DESCRIPTION OF ILLUSTRATION

The accompanying photograph illustrates the new variety and shows the flowering thereof from bud to full bloom depicted in color as nearly correct as it is possible to make in a color illustration of the character. Depicted are three solid blooms between 12A and 15B gradually suffusing with between 16B and 27B and two solid blooms also between 12A and 15B gradually suffusing with between 16B and 27B often moderately suffused with between 46C and 46D to as dark as between 46B and 45B representative of flowers during different stages of bloom. The branches used for the photograph came from 3 to 4 year-old rose plants of the new variety grown outdoors in Pomona, Calif. in the month of November. Throughout this specification, color references and/or values are based upon The Colour Chart of The Royal Horticultural Society (1966) except where common terms of color definition are employed.

DESCRIPTION OF THE NEW VARIETY

The following description is of 3 to 4 year-old rose plants of the new variety grown outdoors in Pomona, Calif. in the month of November. Phenotypic expression may vary with environmental, cultural and climatic conditions, as well as differences in conditions of light and soil.

FLOWER

The new variety usually bears its flowers singly. Flowers are borne on strong irregular length stems, short to moderately long (about 13 to about 75 cm.). Outdoors, the plant blooms abundantly and nearly continuously during the growing season. The flowers have a slight fruity to somewhat tea fragrance.

BUD

The peduncle is about 3.2 to about 5.3 cm. in length, of average to somewhat heavy caliper (about 0.3 to about 0.4 cm. in diameter), and usually erect. It is moderately rough, with many stipitate glands and some hairs. Peduncle color is between 146B and 147B often moderately suffused, especially on the side exposed to the sun, with between 187B and 187A.

Before the calyx breaks, the bud is about 1.4 to about 1.8 cm. in diameter at the widest point, about 1.6 to about 2.3 cm. in length, and pointed to somewhat ovoid in shape. The surface of the bud bears between 11 to 17 foliaceous appendages with some stipitate glands and hairs, usually with moderately stout much cut foliaceous parts extending beyond the tip of the bud about ¾ or more of its length. Bud color is between 137B and 147B sometimes moderately suffused, especially on the side exposed to the sun, with between 187B and 187A.

The sepals are about 2.3 to about 4.5 cm. in length and about 0.6 to about 1.1 cm. in width at the widest point. The outer surface color of the sepal is between 137B and 147B sometimes moderately suffused, especially on the side exposed to the sun, with between 187B and 187A. The outer surface of the sepal is moderately smooth and bears between 0 to 6 foliaceous appendages with some stipitate glands and hairs. The inner surface color of the sepal is near 146C broadly bordered by near 137A. The inner surface of the sepal is covered with fine wooly tomentum; sepal margins are lined with many stipitate glands and hairs.

The receptacle of the flower is of medium to somewhat long length (about 0.5 to about 0.8 cm.) and moderately thin to average in caliper (about 0.8 to about 1.1 cm. in diameter). The receptacle is cup-shaped in form. Its surface is smooth with some hairs and with somewhat thin fleshy walls. The receptacle color is between 144A and 147B sometimes lightly suffused, especially on the side exposed to the sun, with between 187B and 187A.

As the petals open (after the calyx breaks), the bud is about 1.8 to about 2.4 cm. in diameter at the widest point, about 2.2 to about 3.3 cm. in length, and ovoid in form. The color of the under surfaces of the newly opened petals is between 31A and 23A often heavily suffused with between 46B and 45B to as dark as between 53A and 53B. At the point where the petal attaches, there is a large zone of between 5B and 6B. The color of the upper surfaces of the newly opened petals is between 28A and 32A sometimes moderately suffused with between 46C and 45C to as dark as between 46A and 45A. At the point where the petal attaches, there is a large zone of between 12A and 21B.

BLOOM

When fully open, the bloom ranges from about 8.7 to about 12.6cm. in diameter. Petalage is double with about 27 to 35 petals and about 2 to 6 petaloids irregularly arranged. When partially open, the bloom form is moderately high centered to somewhat cupped, and the petals are loosely spiraled to somewhat cupped with petal edges moderately reflexed outward. When fully open, the bloom form is cupped, and the petals are loosely cupped to somewhat undulated with petal edges moderately reflexed outward.

PETALS

The substance of the petals is moderately heavy and of medium thickness, with upper surfaces moderately shiny to somewhat satiny and under surfaces moderately shiny. The petals are about 3.7 to about 5.6 cm. in length and about 2.7 to about 6.1 cm. in width at the widest point. Petal margins are entire.

The outer petals are nearly round in shape with rounded to sometimes moderately mucronate apices.

The inner petals are moderately obovate in shape with rounded to sometimes slightly mucronate apices.

Petaloids are about 1.5 to about 3.7 cm. in length and about 0.7 to about 2.1 cm. in width at the widest point. Petaloids are irregularly shaped moderately obovate to somewhat oblanceolate with rounded apices.

NEWLY OPENED FLOWER

The under surface color of the outer petals is between 13B and 21B often heavily suffused on most of the petals' surface with between 46C and 45C to as dark as between 53A and 53B. There is no visible change in coloration at the point where the petal attaches. The color at the base of the upper surfaces of the outer petals is between 14B and 13A gradually suffusing with between 17B and 21B often lightly suffused with between 46C and 45C. There is no visible change in coloration at the point where the petal attaches.

The under surface color of the intermediate and inner petals is between 12B and 21B often lightly suffused on most of the petals' surface with between 46C and 45C. The color at the base of the upper surfaces of the intermediate and inner petals is between 14B and 13A gradually suffusing with between 16A and 21B.

The under and upper surface colors of the petaloids are similar in coloration to the upper and under surfaces of the intermediate and inner petals.

The general tonality of the newly opened flower is between 16A and 21B.

THREE-DAY-OLD FLOWER

The under surface color of the outer petals is between 12B and 13C often moderately suffused on most of the petals' surface with between 53C and 53D to as dark as between 53A and 53B. There is no visible change in coloration at the point where the petal attaches. The upper surface color of the outer petals is between 12A and 15B gradually suffusing with between 16B and 27B often moderately suffused with between 46C and 46D to as dark as between 46B and 45B during different stages of bloom. There is no visible change in coloration at the point where the petal attaches.

The under surface color of the intermediate and inner petals is between 10A and 11A often lightly suffused on most of the petals' surface with between 53C and 53D. The color at the base of the upper surfaces of the intermediate and inner petals is between 7C and 15B gradually suffusing with between 16B and 27B often moderately suffused with between 46C and 46D to as dark as between 46B and 45B.

The under and upper surface colors of the petaloids are similar in coloration to the upper and under surfaces of the intermediate and inner petals.

The general tonality of the three-day-old flower is between 16B and 27B often moderately suffused with between 46C and 46D to as dark as between 46B and 45B.

On the spent bloom, the petals usually drop off cleanly.

In November in Pomona, Calif., blooms on the bush growing outdoors generally last about four to five days. Cut roses from plants grown outdoors and kept at normal indoor living temperatures generally last about four to five days.

MALE REPRODUCTIVE ORGANS

Stamens are many in number (average about 125) and are arranged regularly about the pistils; a few are mixed with petaloids. The filaments are of medium to somewhat long length (about 0.5 to about 1.1 cm.) most with anthers. Filaments are between 12A and 13B in color. The anthers are of medium to somewhat large size for the class and all open approximately at the same time. Anther color when immature is near 23A on the external part and near 12D on the internal part. Anther color at maturity is near 165B on the external part and near 200A on the internal part. Pollen is moderate and between 18A and 20B in color.

FEMALE REPRODUCTIVE ORGANS

Pistils vary in number (average about 95). The styles are moderately even, somewhat long in length (about 0.4 to about 0.8 cm.), moderately heavy in caliper, and loosely bunched to somewhat separated. Stigma color is between 8B and 5C. Style color is between 154C and 150D often moderately suffused, mostly on the upper half, with between 53B and 53C. Ovaries are usually all enclosed in the calyx.

Hips are of average to somewhat long length (about 1.8 to about 2.5 cm.), globular in form with a flat top, and between 34B and 33B in color when ripe. The hip surface is smooth with thick fleshy walls. The sepals are moderately permanent and usually straight in shape.

The seeds are irregularly rounded, smooth in texture, approximately 17 to about 31 per hip, about 0.5 to about 0.8 cm. in diameter at the widest point and between 164B and 165C in color.

FOLIAGE

The compound leaves are usually comprised of three to seven leaflets and are borne abundantly. The seven-leaflet leaves are about 9.9 to about 18.3 cm. in length and about 7.0 to about 11.8 cm. in width at the widest point, moderately leathery to somewhat crisp in texture, and glossy in finish on the upper side and slightly glossy to matte in finish on the under side. The leaves have a pinnate venation pattern. The terminal leaflets are about 3.9 to about 7.7 cm. in length and about 2.5 to about 5.3 cm. in width at the widest point, shaped ovate with acute apices and rounded bases. Their margins are usually simply serrate.

The upper surface color of the mature leaf is between 139A and 147A. The under surface color of the mature leaf is between 147B and 137C. The under and upper colors of the leaf veins on the mature leaf are similar in coloration to the upper and under surfaces colors of the mature leaf. The upper surface color of the young leaf is between 137A and 147B, often moderately suffused with between 187B and 187A. The under surface color of the young leaf is between 138B and 139C, often moderately suffused with between 187B and 187A. The under and upper colors of the leaf veins on the young leaf are similar in coloration to the upper and under surfaces colors of the young leaf.

The rachis is somewhat heavy in caliper and rough. The upper side is shallowly grooved with few hairs and stipitate glands on the edges of the grooves. The under side of the rachis is rough with some stipitate glands and few small prickles. The rachis color is near 146D on the under side and near 137B on the upper side often moderately suffused on the young leaves with between 187B and 183A.

The stipules are about 1.4 to about 2.2 cm. in length and moderately wide (about 0.4 to about 0.9 cm.) with long straight points that usually turn out at an angle of more than 45 degrees and sometimes recurve toward the stem. The under and upper surface color of the stipule is between 137A and 137B often moderately suffused on the young leaves with between 187C and 183B.

The petiole is somewhat heavy in caliper and rough. The upper side is shallowly grooved with few hairs and stipitate glands on the edges of the grooves. The under side of the petiole is rough with some stipitate glands and few small prickles. The petiole is about 0.7 to about 1.4 cm. in length and about 0.15 to about 0.2 cm in width at the widest point. The petiole color is near 146D on the under side and near 137B on the upper side often moderately suffused on the young leaves with between 187B and 183A.

The plant displays an above average degree of resistance to powdery mildew and rust as compared to other commercial varieties grown under comparable conditions in Pomona, Calif. The plant's winter hardiness and drought/heat tolerance are yet to be determined.

GROWTH

The plant has an upright moderately spreading tall growing habit (about 120 to about 200 cm. in height and about 180 to about 210 cm. spread at the widest point), with full branching. It displays vigorous growth and the canes are of medium caliper for the class (about 1.7 to about 2.5 cm. in diameter at the widest point).

The color of the major stems is between 147B and 146B. They bear some large prickles that are about 0.7 to about 1.1 cm. in length. The large prickles are almost straight to slightly angled downward with a short broad oval base; prickle color is between 200D and 165A. The major stem bears some small prickles of similar shape and coloration.

The color of the branches is between 137C and 147B sometimes lightly suffused with between 187A and 187B. They bear some large prickles which are of similar size and shape to the large prickles on the major stems; prickle color is near 152B sometimes lightly suffused with between 187C and 187D. The branches bear few small prickles of similar shape and coloration.

The color of the new shoots is between 146B and 147B often heavily suffused with between 187B and 187A. They bear some large prickles which are of similar size and shape to the large prickles on the major stems; prickle color is near 152B often heavily suffused with between 187B and 187C. The shoots bear few small prickles of similar shape and coloration.

I claim:

1. A new and distinct Hybrid Tea rose plant of the variety substantially as described and illustrated herein.

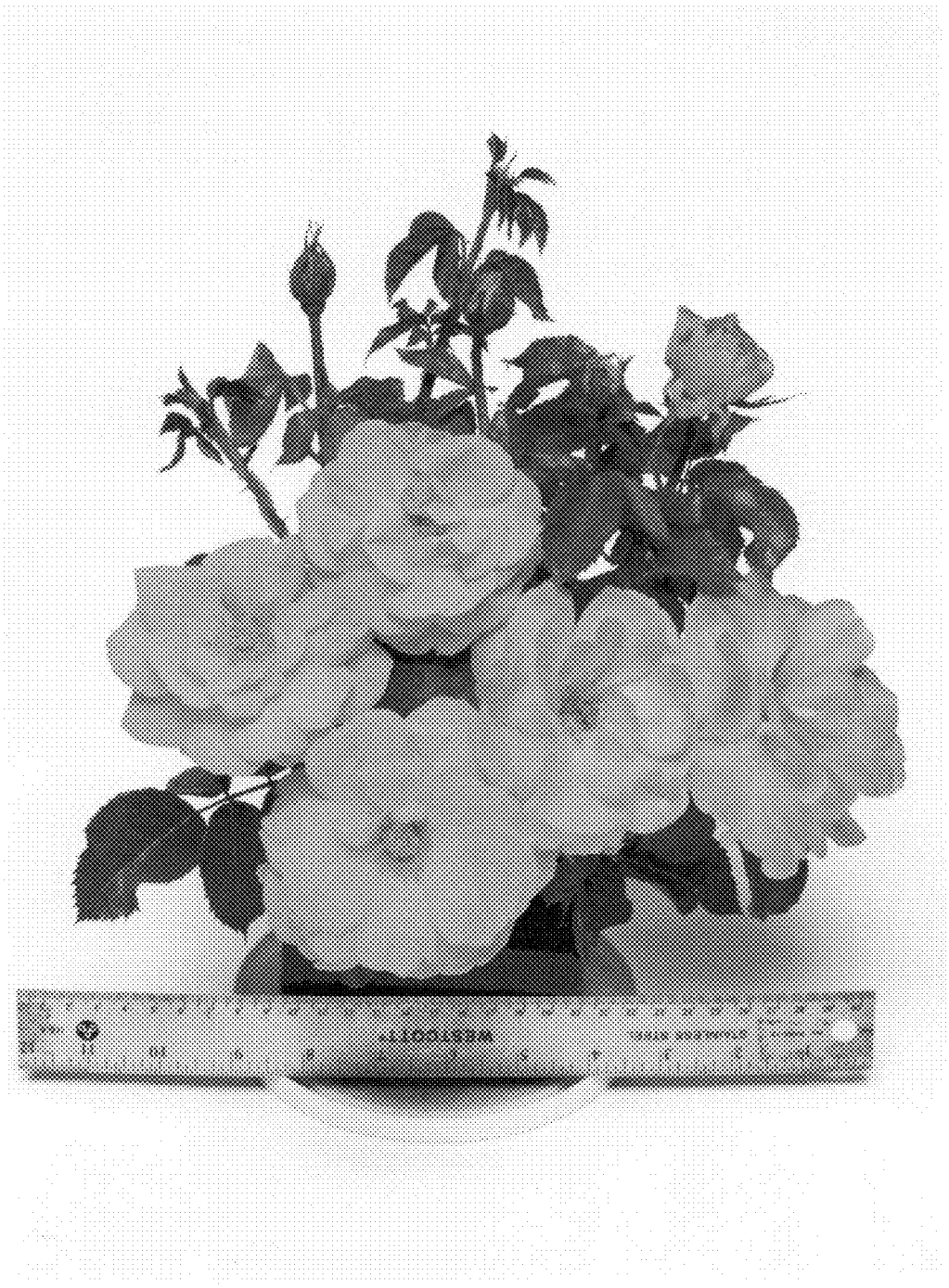

* * * * *